(12) United States Patent
Justis et al.

(10) Patent No.: US 6,761,719 B2
(45) Date of Patent: *Jul. 13, 2004

(54) SUPERELASTIC SPINAL STABILIZATION SYSTEM AND METHOD

(75) Inventors: Jeff R. Justis, Cordova, TN (US); Michael C. Sherman, Memphis, TN (US)

(73) Assignee: SDGI Holdings, Inc., Wilmington, DE (US)

(*) Notice: Subject to any disclaimer, the term of this patent is extended or adjusted under 35 U.S.C. 154(b) by 159 days.

This patent is subject to a terminal disclaimer.

(21) Appl. No.: 09/960,770

(22) Filed: Sep. 21, 2001

(65) Prior Publication Data

US 2002/0013586 A1 Jan. 31, 2002

Related U.S. Application Data

(63) Continuation of application No. 09/516,946, filed on Mar. 1, 2000, now Pat. No. 6,293,949.

(51) Int. Cl.$^7$ .............................................. A61B 17/56
(52) U.S. Cl. ........................................... 606/61; 606/69
(58) Field of Search ............................. 606/61, 69, 70, 606/71, 76, 78; 623/17.11, 17.15, 17.16

(56) References Cited

U.S. PATENT DOCUMENTS

| | | | |
|---|---|---|---|
| 3,786,806 A | | 1/1974 | Johnson et al. |
| 4,743,260 A | | 5/1988 | Burton |
| 5,041,113 A | | 8/1991 | Biedermann et al. |
| 5,092,866 A | | 3/1992 | Breard et al. |
| 5,180,381 A | | 1/1993 | Aust et al. |
| 5,387,213 A | | 2/1995 | Breard et al. |
| 5,415,661 A | | 5/1995 | Holmes |
| 5,540,689 A | * | 7/1996 | Sanders et al. ............... 606/61 |
| 5,551,871 A | | 9/1996 | Besselink et al. |

(List continued on next page.)

FOREIGN PATENT DOCUMENTS

SU 940759 7/1982

OTHER PUBLICATIONS

"The Use of a Memory Shape Staple in Cervical Anterior Fusion", by Olivier Ricart, Shape Memory and Superelastic Technologies ©1997, pp. 623–626.

(List continued on next page.)

*Primary Examiner*—Eduardo C. Robert
(74) *Attorney, Agent, or Firm*—Woodard, Emhardt, Moriarity, McNett & Henry LLP (57) ABSTRACT

A device for stabilizing at least a portion of the spinal column, including a longitudinal member sized to span a distance between at least two vertebral bodies and being at least partially formed of a shape-memory material exhibiting pseudoelastic characteristics at about human body temperature. A number of bone anchors are used to secure the longitudinal member to each of the vertebral bodies. The longitudinal member is reformed from an initial configuration to a different configuration in response to the imposition of stress caused by relative displacement between the vertebral bodies, and recovers toward the initial configuration when the stress is removed to thereby provide flexible stabilization to the spinal column. During reformation of the longitudinal member, at least a portion of the shape-memory material transforms into stress-induced martensite. In a particular aspect of the invention, the longitudinal member is a plate having a central portion at least partially formed of the shape-memory material, and a pair of connection portions disposed at opposite ends of the central portion for connection to each of the vertebral bodies. The central portion of the plate defines a number of alternating ridges and grooves along a length thereof having an initial amplitude corresponding to the initial configuration and a different amplitude corresponding to the different configuration.

30 Claims, 9 Drawing Sheets

U.S. PATENT DOCUMENTS

| | | | |
|---|---|---|---|
| 5,597,378 A | | 1/1997 | Jervis |
| 5,616,144 A | | 4/1997 | Yapp et al. |
| 5,658,286 A | * | 8/1997 | Sava ............................ 606/61 |
| 5,728,098 A | | 3/1998 | Sherman et al. |
| 5,766,218 A | | 6/1998 | Arnott |
| 5,776,162 A | | 7/1998 | Kleshinski |
| 5,779,707 A | | 7/1998 | Bertholet et al. |
| RE36,221 E | | 6/1999 | Breard et al. |
| 5,954,725 A | | 9/1999 | Sherman et al. |
| 6,132,434 A | | 10/2000 | Sherman et al. |
| 6,210,413 B1 | | 4/2001 | Justis et al. |
| 6,254,602 B1 | | 7/2001 | Justis |
| 6,273,888 B1 | | 8/2001 | Justis |
| 6,287,311 B1 | | 9/2001 | Sherman et al. |
| 6,293,949 B1 | * | 9/2001 | Justis et al. .................... 606/61 |
| 6,296,643 B1 | | 10/2001 | Hopf et al. |
| 6,299,613 B1 | | 10/2001 | Ogilvie et al. |
| 6,325,805 B1 | | 12/2001 | Ogilvie et al. |
| 6,436,099 B1 | | 8/2002 | Drewry et al. |
| 6,454,773 B1 | | 9/2002 | Sherman et al. |
| 2003/0204189 A1 | * | 10/2003 | Cragg .......................... 606/61 |

OTHER PUBLICATIONS

"The Use of Nickel–Titanium Alloy in Orthopedic Surgery in China", by Paul Pang–Fu Kuo, MD et al., Orthopedics, Jan. 1989, vol. 12/No. 1, pp. 111–116.

"Using the Shape Recovery of Nitinol in the Harrington Rod Treatment of Scoliosis", by M.A. Schmerling et al., vol. 10, pp. 879–892, 1976.

"Medical Applications of Ni–Ti Alloys in China", by Shibi Lu, M.D., pp. 445–451.

The Use of Ni–Ti as an Implant Material in Orthopedics, by Dr. J. Haasters, Prof. G. v.Salis–Solio, & Dr. G. Bensmann, pp. 426–444.

"Shape Memory and Super–elasticity Effects in NiTi Alloys", by Yuichi Suzuki, Excerpt from Titanium and Zirconium, vol. 30, No. 4, Oct. 1982.

"TiNi–alloy with super elasticity", (Transplantation of the human malignant bone and soft part tumors to nude mice), *Orthopedic Surgery*, vol. 32, No. 1, Jan. 1981.

SMST–97, Proceedings of the Second International Conference on Shape Memory and Superelastic Technologies, Mar. 2–6, 1997.

* cited by examiner

SUPERELASTIC SPINAL STABILIZATION SYSTEM AND METHOD

The present Application is a continuation of pending U.S. patent application Ser. No 09/516,946, filed Mar. 1, 2000 now U.S. Pat. No. 6,293,949, the contents of which are hereby incorporated by reference.

FIELD OF THE INVENTION

The present invention relates generally to the field of instrumentation and systems for treatment of the spine, and more particularly to a device for flexibly stabilizing the cervical spine.

BACKGROUND OF THE INVENTION

As with any bony structure, the spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two adjacent vertebrae and the disc tissue or disc space therebetween), and especially those affecting disc tissue, it has long been known to remove some or all of a degenerated, ruptured or otherwise failing disc. In cases in which intervertebral disc tissue is removed or is otherwise absent from a spinal motion segment, corrective measures are indicated to insure the proper spacing of adjacent vertebrae formerly separated by the removed disc tissue.

Commonly, the adjacent vertebrae are fused together using a graft structure formed of transplanted bone tissue, an artificial fusion element, or other suitable compositions. Elongated rigid plates have been helpful in the stabilization and fixation of the spine when used alone or in conjunction with a grafting procedure, especially in the thoracic and lumbar regions of the spine. These plating systems also have the potential advantage of increasing union rates, decreasing graft collapse, minimizing subsequent kyphotic deformity, and decreasing the need for bulky or rigid postoperative immobilization. Additionally, rigid internal fixation systems may improve the overall quality of life of the patient and may provide the opportunity for earlier rehabilitation.

The plating techniques described above have also found some level of acceptance by surgeons specializing in the treatment of the cervical spine. The cervical spine can be approached either anteriorly or posteriorly, depending upon the spinal disorder or pathology to be treated. Many well-known surgical exposure and fusion techniques of the cervical spine are described in the publication entitled *Spinal Instrumentation*, edited by Drs. Howard An and Jerome Cotler. The primary focus of cervical plating systems has been to restore stability and increase the stiffness of an unstable spinal motion segment. During the development of cervical plating systems, various needs have been recognized. For example, the system should provide strong mechanical fixation that can control movement of the vertebral segments. The system should also be able to maintain stress levels below the endurance limits of the plate material, while at the same time exceeding the strength of the anatomic structures or vertebrae to which the plating system is engaged. Additionally, the system should preferably be capable of accommodating for the natural movement of the vertebrae relative to one another, including torsional movement during rotation of the spine and translational movement during flexion or extension of the spine.

There is increased concern in the spinal medical community that anterior or posterior plating systems may place excessive loads on the vertebrae or graft structure in response to small degrees of spinal motion. See, e.g., K. T. Foley, D. J. DiAngelo, Y. R. Rampersaud, K. A. Vossel and T. H. Jansen, *The In Vitro Effects of Instrumentation on Multi-level Cervical Strut-Graft Mechanics*, $26^{th}$ Proceeding of the Cervical Spine Research Society, 1998. If the plating system is used in conjunction with grafting, these loads may promote pistoning, which can ultimately lead to degradation or failure of the graft construct. Additionally, even small degrees of spinal motion can cause significant forces to be placed on the spinal plate and the bone anchor devices which attach the plate to the vertebrae, whether they be bone screws, hooks, etc. These forces may lead to failure of the plate or loosening of the points of attachment between the bone anchors and the vertebrae, thus resulting in the potential loss of support by the plate.

Thus, there is a general need in the industry to provide a device for flexibly stabilizing the spine, and in particular the cervical region of the spine. The present invention meets this need and provides other benefits and advantages in a novel and unobvious manner.

SUMMARY OF THE INVENTION

The present invention relates generally to a system for flexibly stabilizing the spine, and more particularly the cervical region of the spine. While the actual nature of the invention covered herein can only be determined with reference to the claims appended hereto, certain forms of the invention that are characteristic of the preferred embodiments disclosed herein are described briefly as follows.

In one form of the present invention, a device is provided for stabilizing at least a portion of a spinal column, comprising a member engaged between at least two vertebral bodies and being at least partially formed of a material capable of exhibiting superelastic characteristics at about body temperature.

In another form of the present invention, a method is provided for stabilizing at least a portion of the spinal column, comprising providing a member at least partially formed of a material capable of exhibiting superelastic characteristics at about body temperature, and engaging the member to at least two vertebral bodies.

In another form of the present invention, a device is provided for stabilizing at least a portion of a spinal column, comprising a rod member engaged to at least two vertebral bodies and being at least partially formed of a shape-memory material capable of exhibiting superelastic characteristics at about body temperature, with the rod member having a length that varies in response to relative displacement between the at least two vertebral bodies.

In another form of the present invention, a system is provided for stabilizing at least a portion of a spinal column, comprising an implant disposed between two adjacent vertebrae, and a member anchored to the two adjacent vertebrae and being at least partially formed of a material capable of exhibiting superelastic characteristics at about body temperature.

It is one object of the present invention to provide a device and method for stabilizing at least a portion of the spine, and more particularly the cervical region of the spine.

Further objects, features, advantages, benefits, and aspects of the present invention will become apparent from the drawings and description contained herein.

BRIEF DESCRIPTION OF THE DRAWINGS

FIG. 5 is a side elevation view of the stabilization plate depicted in FIG. 4a.

FIG. 6 is an end elevation view of the stabilization plate depicted in FIG. 4a.

FIG. 7 is an angled cross-sectional view of the stabilization plate depicted in FIG. 4a, taken along line 7—7 of FIG. 4a.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 1:
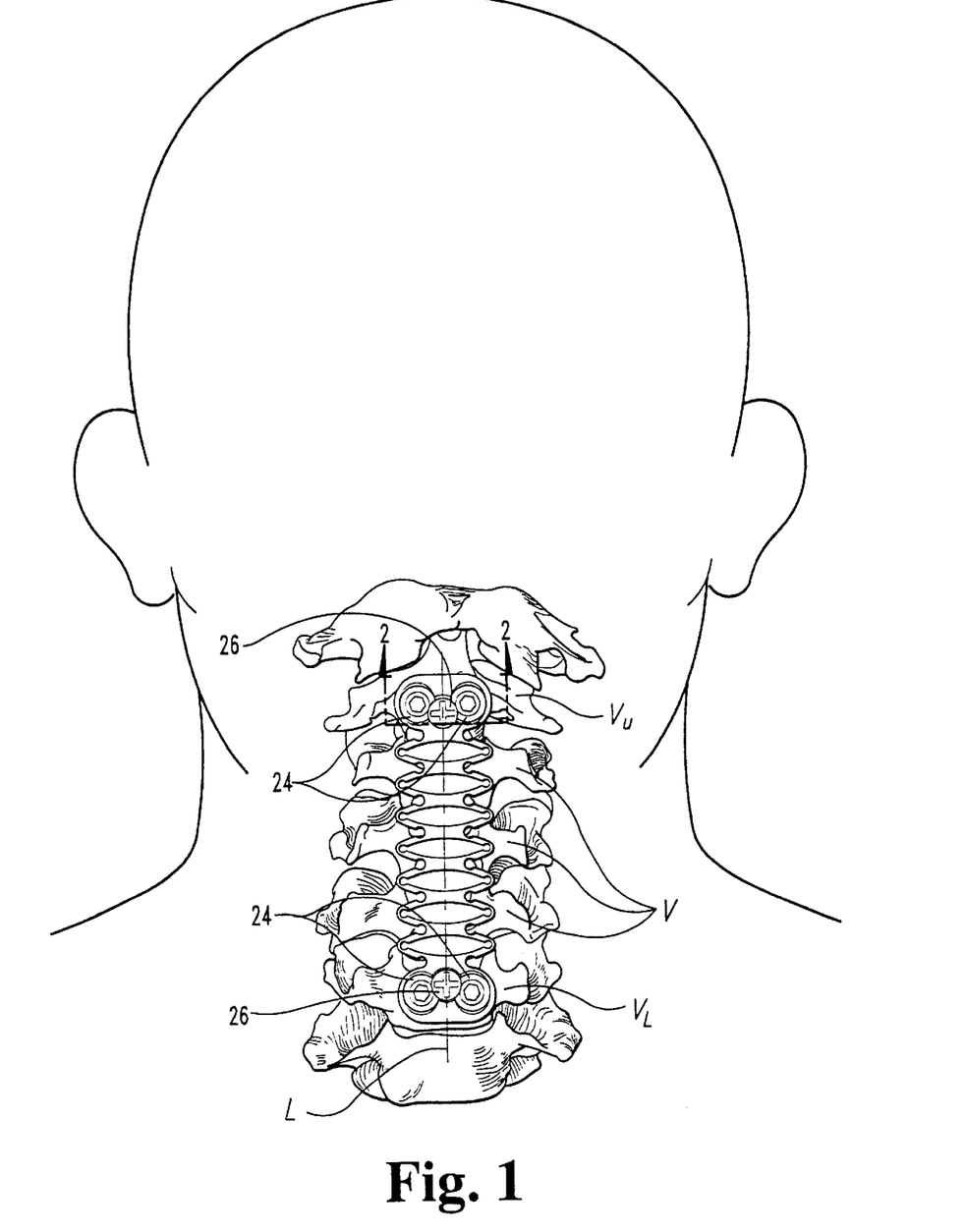
FIG. 1 is an anterior view of the cervical region of the spine showing a spinal stabilization system according to one embodiment of the present invention attached to two cervical vertebrae.
Figure 2:
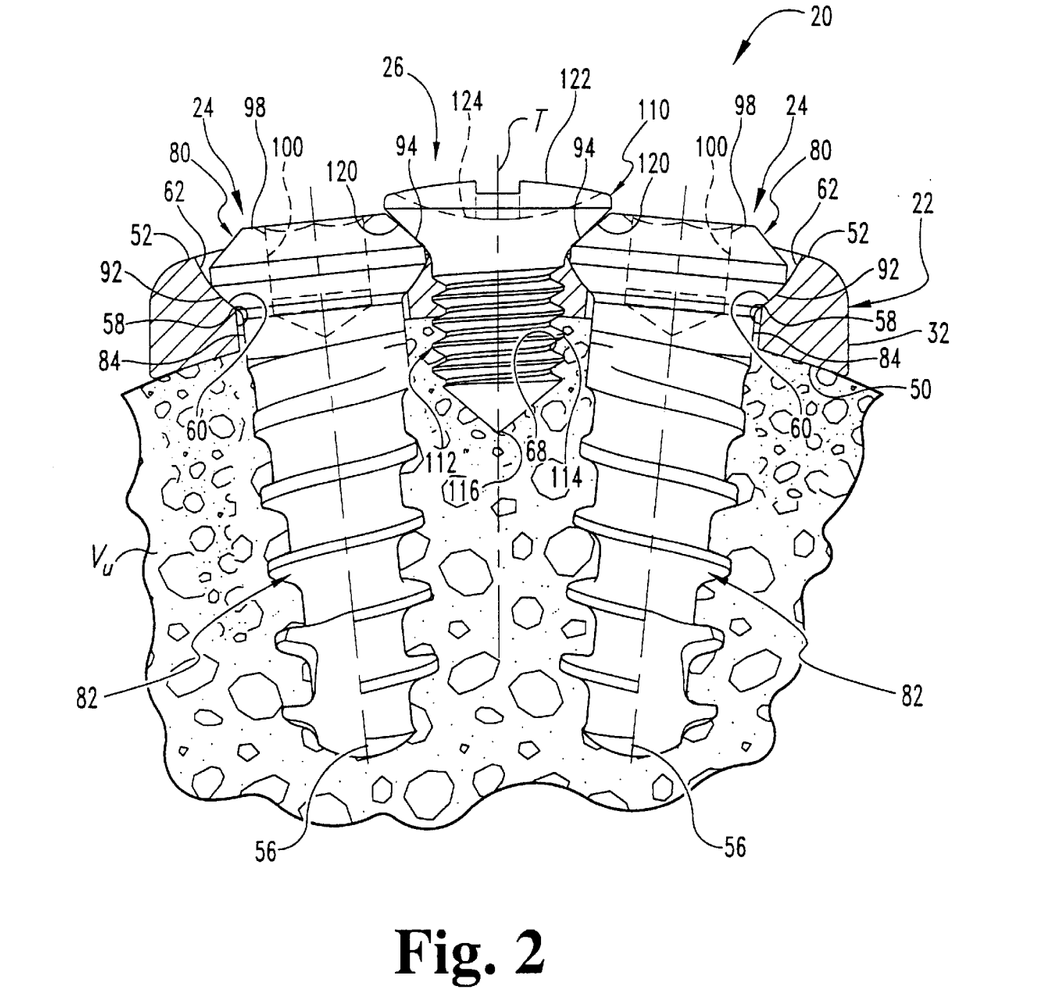
FIG. 2 is a partial cross-sectional view of the spinal stabilization system depicted in FIG. 1, with the screws disposed through holes in the stabilization plate and engaged to a cervical vertebra.
Figure 3:
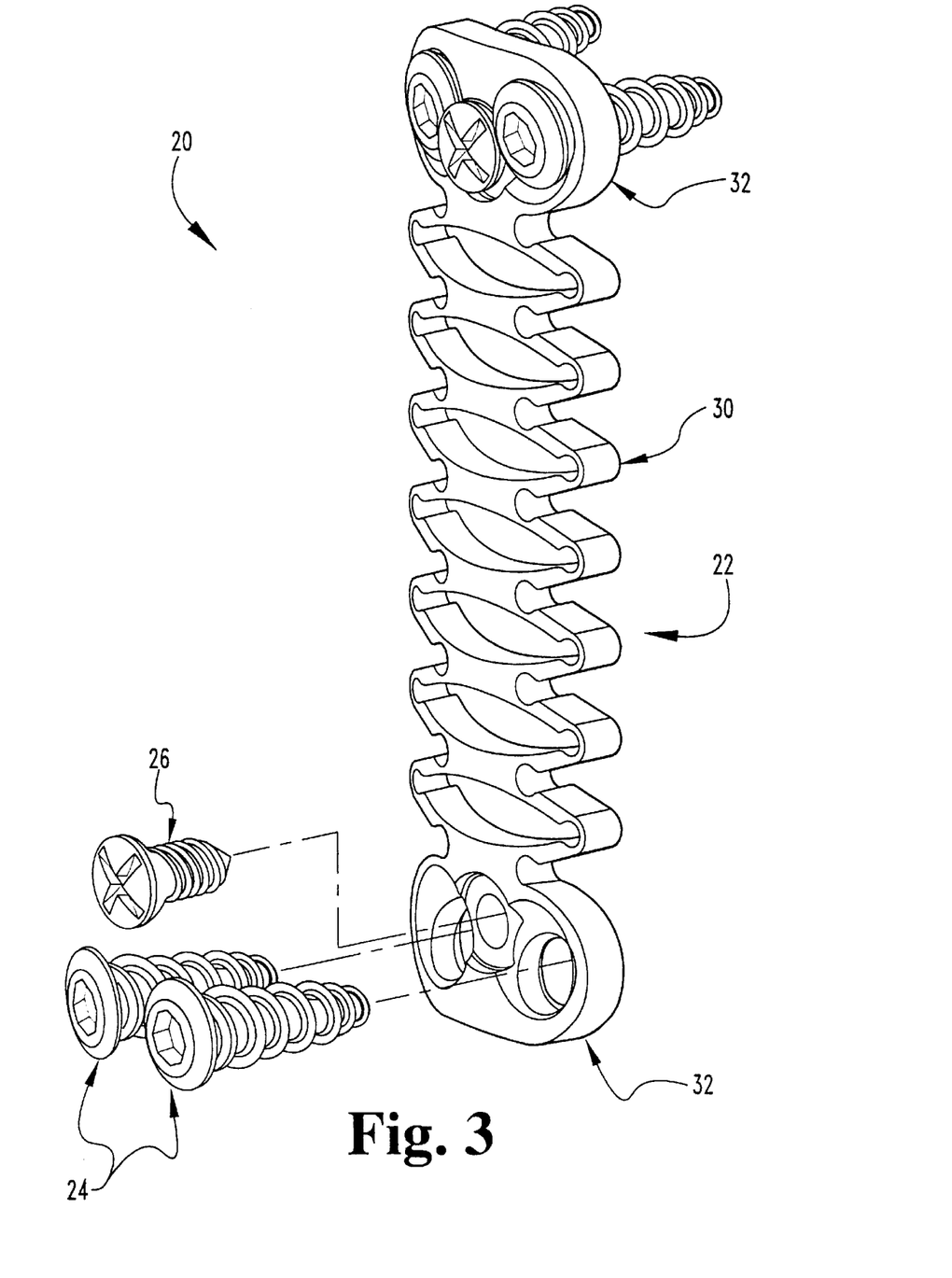
FIG. 3 is a side perspective view of the spinal stabilization system depicted in FIG. 1

FIGS. 1–2 depict a spinal stabilization system 20 according to one embodiment of the present invention for stabilizing at least a portion of the vertebral column. Stabilization system 20 is shown attached to the cervical region of the vertebral column, extending across a plurality of spinal motion segments, such as cervical vertebrae V. However, it should be understood that system 20 may also be utilized in other areas of the spine, such as the thoracic, lumbar, lumbo sacral and sacral regions of the spine. It should also be understood that system 20 can extend across any number of vertebrae V, including two adjacent vertebrae V. Additionally, although system 20 is shown as having application in an anterior approach, system 20 may alternatively be applied in other surgical approaches, such as, for example, a posterior approach.

In a typical grafting procedure, one or more adjacent pairs of vertebra V may be fused together by way of a graft or implant (not shown) positioned in the disc space between the adjacent vertebrae V. The implant may be a bone graft, an artificial fusion device, or any other type of interbody device that is insertable into the disc space to promote fusion between the adjacent vertebrae V. One purpose of the stabilization system 20 is to prevent excessive loads from being placed on the graft structures in response to even small degrees of spinal motion. However, it should be understood that stabilization system 20 can be used in conjunction with fusion or non-fusion treatment of the spine.

Figure 12:
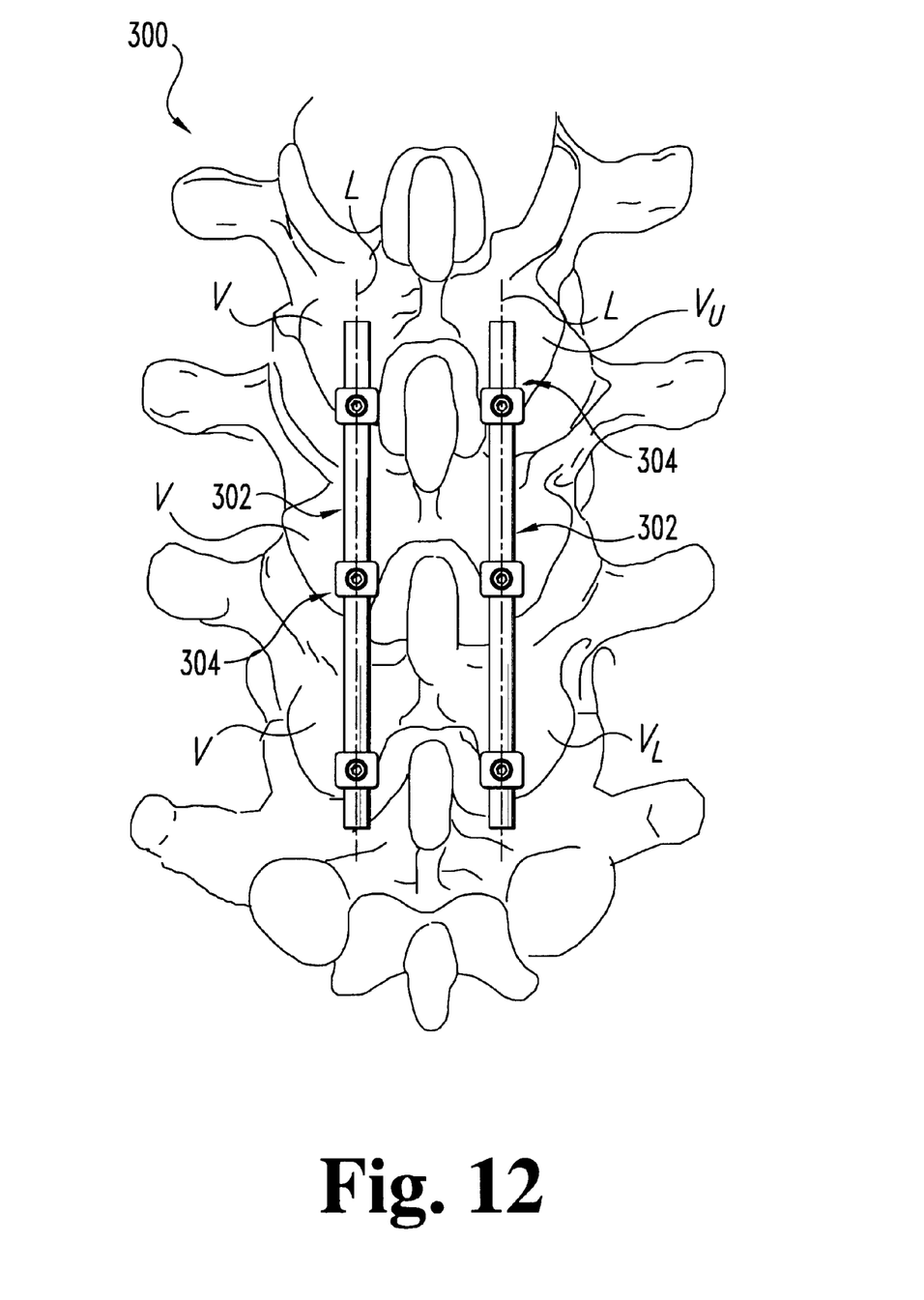
FIG. 12 is a top view of a stabilization rod according to another embodiment of the present invention.

In accordance with the present invention, stabilization system 20 includes an elongate member 22 positioned along a portion of the vertebral column. In the illustrated embodiment, the longitudinal member is an elongated stabilization plate sized to span a distance between at least two vertebrae V. Although elongate member 22 has been illustrated and described as a spinal plate, it should be understood that elongate member 22 can also be configured as a spinal rod 302 (FIG. 12) or any other type of longitudinal element for use in conjunction with a spinal fixation system. It should also be understood that any number of plates 22 or rods 302, including a pair of plates 22 or a pair of rods 302 positioned on opposite sides of the spine, could be used to provide stabilization to the vertebral column. Stabilization plate 22 is secured to the upper and lower vertebrae $V_U$, $V_L$ (FIG. 1) by a plurality of bone anchors, shown in the form of bone screws 24. However, other types of bone anchors are also contemplated, such as, for example, spinal hooks 304 (FIG. 12). A locking device 26 engages the adjacent bone screws 24 to prevent bone screws 24 from loosening and backing out. In the illustrated embodiment, the locking device 26 is a screw extending through each end portion of the plate 22 and into engagement with the heads of adjacent bone screws 24. However, other types of locking devices are also contemplated, such as, for example, a pop rivet, a retainer fabricated from a shape-memory alloy configured to change shape in response to a change in temperature or the release of stress, a locking washer rotatably displaceable between an unlocked position and a locked position, or any other type of locking mechanisms known to those of skill in the art. An example of a locking washer for use with the present invention is disclosed in U.S. patent application Ser. No. 09/399,525 entitled "Anterior Cervical Plating System" filed on Sep. 20, 1999, the contents of which are hereby incorporated by reference. Further details regarding spinal stabilization system 20 are described more fully below.

Referring to FIGS. 3–7, shown therein are various details regarding the stabilization plate 22. Plate 22 has a longitudinal axis L extending along its length and includes an elongated central portion 30 and a pair of connection portions 32 disposed at opposite ends of central portion 30. In the illustrated embodiment, central portion 30 and connection portions 32 are formed integral to plate 22, thus forming a unitary structure or construct. However, it should be understood that connection portions 32 can be formed separate from central portion 30 and attached thereto by any method known to one of ordinary skill in the art, such as, for example, by fastening or welding. Plate 22 is at least partially formed of a shape-memory material that exhibits pseudoelastic characteristics or behavior at about human body temperature, the details of which will be discussed below. It should be understood that the terms "pseudoelastic" and "superelastic" have identical meanings and are used interchangeably throughout this document. In one embodiment of the present invention, the entire plate 22 is formed of the shape-memory material. However, it should be understood that only central portion 30 need be at least partially formed of the shape-memory material, with the connection portion 32 being formed of any suitable biocompatible material, such as, for example, stainless steel or titanium.

SMAs exhibit a "shape-memory" characteristic or behavior in which a particular component formed of a shape-memory alloy ("SMA") is capable of being deformed from an initial "memorized" shape or configuration to a different shape or configuration, and then reformed back toward its initial shape or configuration. The ability to possess shape-memory is a result of the fact that the SMA undergoes a reversible transformation from an austenitic state to a martensitic state. If this transformation occurs due to a change in temperature, the shape-memory phenomena is commonly referred to as thermoelastic martensitic transformation. However, if the martensitic transformation occurs due to the imposition of stress, the shape-memory phenomena is commonly referred to as stress-induced martensitic transformation. The present invention is primarily concerned with stress-induced martensitic transformation.

SMAs are known to display a superelastic phenomena or rubber-like behavior in which a strain attained beyond the elastic limit of the SMA material during loading is recovered during unloading. This superelastic phenomena occurs when stress is applied to an SMA article at a temperature slightly higher than the temperature at which the SMA begins to transform into austenite (sometimes referred to as the transformation temperature or $A_s$). When stressed, the article first deforms elastically up to the yield point of the SMA material (sometimes referred to as the critical stress). However, upon the further imposition of stress, the SMA material begins to transform into stress-induced martensite or "SIM". This transformation takes place at essentially constant stress, up to the point where the SMA material is completely transformed into martensite. When the stress is removed, the SMA material will revert back into austenite and the article will return to its original, pre-programmed or memorized shape. This phenomena is sometimes referred to as super-elasticity or pseudoelasticity. It should be understood that this phenomena can occur without a corresponding change in temperature of the SMA material. Further details regarding the superelastic phenomena and additional characteristics of SIM are more fully described by Yuichi Suzuki in an article entitled *Shape Memory Effect and Super-Elasticity in Ni—Ti Alloys*, Titanium and Zirconium, Vol. 30, No. 4, October 1982, the contents of which are hereby incorporated by reference.

There is a wide variety of shape-memory materials suitable for use with the present invention, including shape-memory metal alloys (e.g., alloys of known metals, such as, for example, copper and zinc, nickel and titanium, and silver and cadmium) and shape-memory polymers. While there are many alloys which exhibit shape-memory characteristics, one of the more common SMAs is an alloy of nickel and titanium. One such alloy is nitinol, a bio-compatible SMA formed of nickel and titanium. Nitinol is well suited for the particular application of the present invention because it can be programmed to undergo a stress-induced martensitic transformation at about normal human body temperature (i.e., at about 35–40 degrees Celsius). Moreover, nitinol has a very low corrosion rate and excellent wear resistance, thereby providing an advantage when used as a support structure within the human body. Additionally, implant studies in animals have shown minimal elevations of nickel in the tissues in contact with the nitinol material. It should be understood, however, that other SMA materials that exhibit superelastic characteristics are contemplated as being within the scope of the invention.

The central portion 30 of plate 22 is at least partially formed of an SMA material and has an initial or "memorized" shape or configuration (see FIG. 4a), and a different shape or configuration (FIG. 4b) when deformed through the imposition of stress onto plate 22. If the central portion 30 is reshaped or deformed while at a temperature above the transformation temperature $A_s$, the central portion 30 will automatically recover toward its initial shape or configuration when the stress is removed from plate 22. In one embodiment of the present invention, the plate 22 is secured to the upper and lower vertebrae $V_u$, $V_l$ while in a substantially unstressed initial configuration where virtually all of the SMA material is in an austenitic state. Upon the imposition of stress onto plate 22, caused by relative movement between the upper and lower vertebrae $V_u$, $V_l$, at least a portion of the SMA material is transformed into reversible stress-induced martensite. Upon the reduction or removal of stress, at least a portion of the SMA material is transformed back into austenite. It should be understood that the plate 22 may be pre-stressed prior to being secured to the upper and lower vertebrae $V_u$, $V_l$, thus initially transforming a portion of the SMA material from austentite into SIM. In this case, the SMA material will never attain an entirely austenitic state when the stress imposed onto plate 22 by the upper and lower vertebrae Vu, Vl is removed.

Figure 4A:
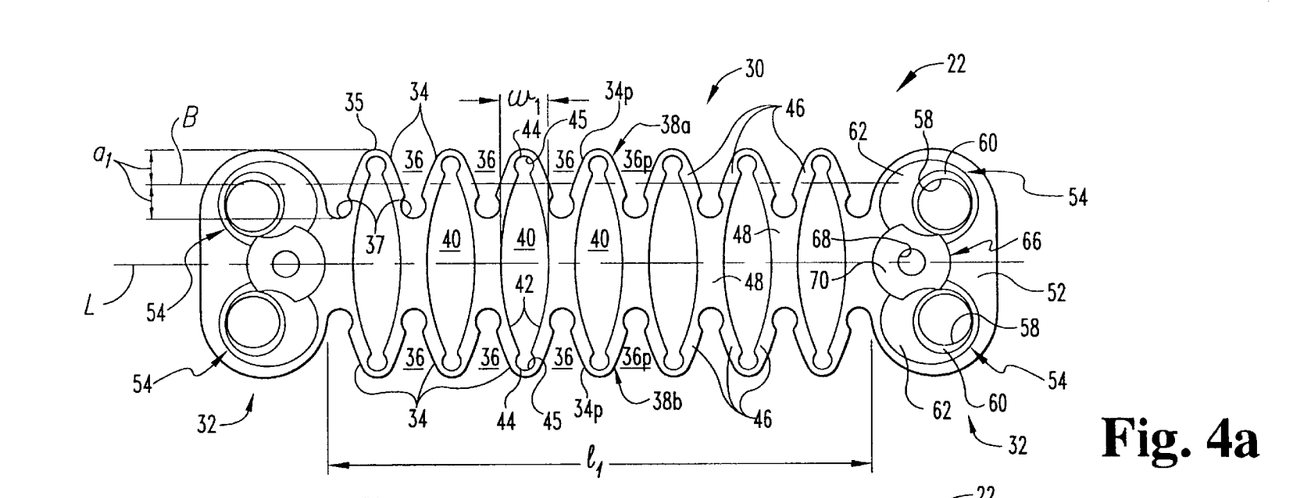
FIG. 4a is a top view of a stabilization plate according to an embodiment of the present invention, shown in an unstressed configuration.

Referring specifically to FIG. 4a, central portion 30 is shown in an initial, unstressed configuration. Central portion 30 has an accordion-like shape, defining a series of alternating ridges 34 and grooves 36 extending along longitudinal axis L and facing laterally outward relative to longitudinal axis L. When in its initial configuration, central portion 30 has an initial, unstressed length $l_1$. Preferably, each of the alternating ridges 34 and grooves 36 has a substantially triangular shape, with the outermost tip 35 of ridges 34 being rounded to avoid trauma to adjacent tissue, and the innermost portion of grooves 36 defining a partially cylindrical surface 37. However, it should be understood that ridges 34 and grooves 36 can take on other shapes as well, such as, for example, an arcuate shape, an undulating curve shape, or a square or rectangular shape. When central portion 30 is in its initial configuration, each of the ridges 34 and grooves 36 have an initial amplitude $a_1$, as measured from base line B to the outermost tip 35 and the innermost point of cylindrical surface 37. Preferably, the partially cylindrical surface 37 has a diameter somewhat larger than the minimum distance between adjacent ridges 34.

In the illustrated embodiment, a number of the alternating ridges 34 and grooves 36 are defined along each of the laterally facing sides 38a, 38b of central portion 30, with the ridges and grooves defined along side 38a being disposed laterally opposite respective ones of the ridges and grooves defined along side 38b, thereby defining laterally opposing pairs of ridges $34_p$ and laterally opposing pairs of grooves $36_p$. A number of openings or slots 40 extend through central portion 30 intermediate the laterally opposing pairs of ridges $34_p$. Preferably, slots 40 have a substantially oval shape, with each of the slots 40 having laterally extending side walls defining opposing concave surface 42 and an initial slot width $w_1$ when central portion 30 is in its initial, unstressed configuration. However, it should be understood that slots 40 can take on other shapes as well, such as, for example, circular, elliptical, diamond or other geometric shapes as would occur to one of ordinary skill in the art. Slots 40 span virtually the entire distance between the opposing pairs of ridges $34_p$, having opposing ends 44 positioned proximately adjacent the outermost tips 35 of opposing pairs of ridges $34_p$. In a preferred embodiment, the opposing ends 44 of slots 40 each define a partially cylindrical surface 45. Preferably, the partially cylindrical surface 45 has a diameter somewhat larger than the minimum distance between the opposing concave surfaces 42. The configuration of central portion 30 can alternatively be described as having a pair of laterally opposing thin strips of material 46 extending along longitudinal axis L, each having a zig-zag or corrugated shape and being linked together by a number of laterally extending linking portions 48.

Figure 4B:
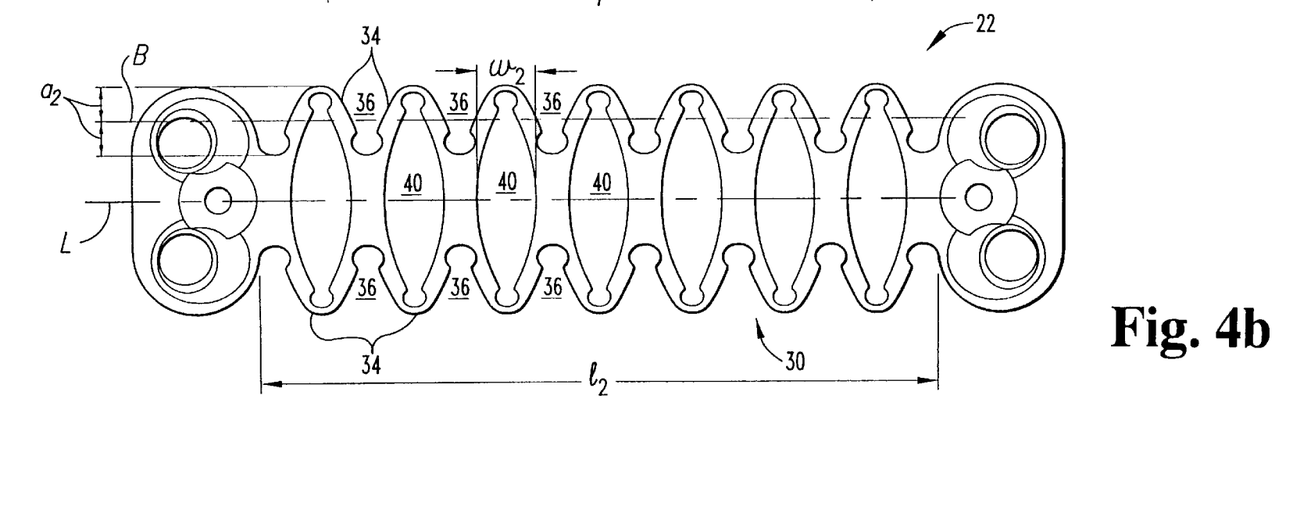
FIG. 4b is a top view of the stabilization plate depicted in FIG. 4a, shown in a stressed configuration.

Referring now to FIG. 4b, central portion 30 is shown reformed from the initial shape or configuration illustrated in FIG. 4a to a different, stressed shape or configuration, such reformation occurring in response to the imposition of stress caused by relative displacement between the upper and lower vertebrae $V_u$, $V_l$ (FIG. 1). This relative displacement can arise through translational movement of upper and lower vertebrae $V_u$, $V_l$, as occurring during either flexion or extension of the spinal column, or through torsional movement, as occurring during rotation of the spinal column. The imposition of stress onto central portion 30 causes at least a portion of the shape-memory material to transform into reversible stress-induced martensite. When deformed into its different configuration, central portion 30 has a different, stressed length $l_2$, ridges 34 and grooves 36 have a different amplitude $a_2$, and slots 40 are reshaped to define a different slot width $w_2$. In the illustrated embodiment, central portion 30 is elongated or lengthened when stressed, thus increasing length $l_2$ and slot width $w_2$ while decreasing the amplitude $a_2$. However, it should be understood that central portion 30 could alternatively be compressed or shortened when stressed, thus decreasing length $l_2$ and slot width $w_2$ while increasing the amplitude $a_2$.

Figure 7:
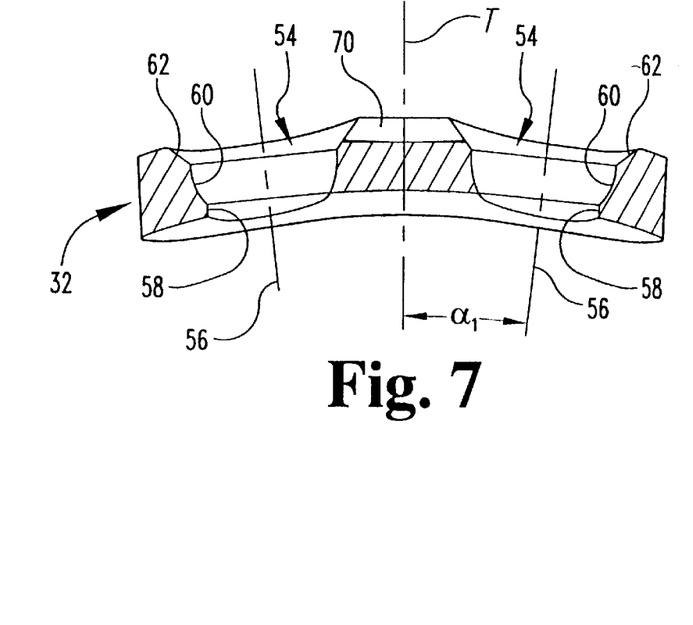

Referring collectively to FIGS. 4a and 7, shown therein are various details regarding the connection portions 32. Each of the connection portions 32 has an inner surface 50 and an oppositely facing outer surface 52. When plate 22 is secured to the spinal column (FIGS. 1 and 2), the inner surface 50 abuts the upper and lower vertebrae $V_u$, $V_l$. Inner surface 50 defines a concave lateral curvature C (FIG. 6) extending along the longitudinal axis L. Lateral curvature C preferably corresponds to the anatomical curvature of the anterior, outer surfaces of upper and lower vertebrae $V_u$, $V_l$. Outer surface 52 preferably defines a convex surface extending along longitudinal axis L to reduce the amount of trauma to the adjacent soft tissue when plate 22 is secured to the spinal column. Preferably, the central portion 30 of plate 22 defines a corresponding concave lateral curvature C along inner surface 51 and a corresponding convex outer surface 53. However, it should be understood that the central portion 30 and the connection portions 32 can be individually configured to accommodate the specific spinal anatomy and vertebral pathology involved in any particular application of stabilization system 20.

Figure 5:
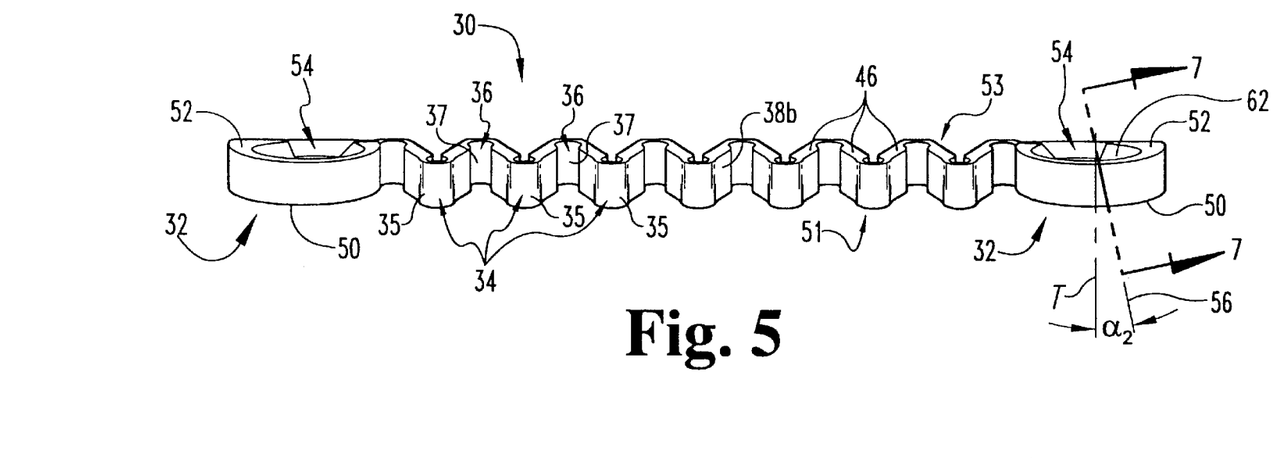
Figure 6:
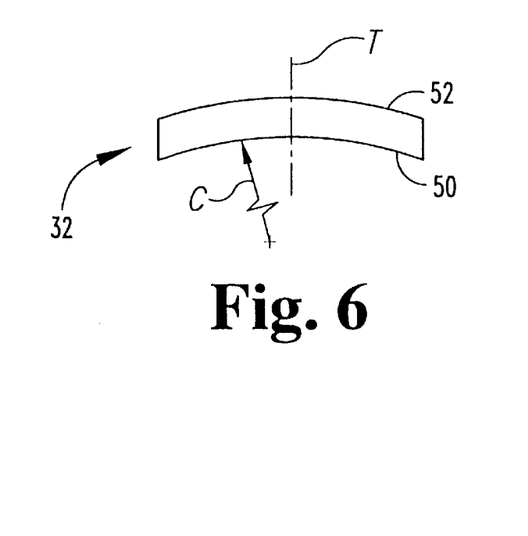

Each of the connection portions 32 includes a pair of openings 54 extending between the inner and outer surfaces 50, 52 along an axis 56 and configured to receive a respective one of the bone screws 24 therein. In the illustrated embodiment, the axis 56 of openings 54 extends inwardly toward transverse axis T at an angle $\alpha_1$ (FIG. 7) and outwardly toward the end of connection portion 32 at an angle $\alpha_2$ (FIG. 5). In one specific embodiment, angle $\alpha_1$ is approximately 6 degrees and angle $\alpha_2$ is approximately 12 degrees; however, other angles $\alpha_1$, $\alpha_2$ are also contemplated as being within the scope of the present invention. Preferably, openings 54 are identical in size and configuration, and are located symmetrically about longitudinal axis L. However, it should be understood that other sizes and configurations of openings 54 are also contemplated and that a single opening 54 could alternatively be defined in each of the connection portions 32. Each of the openings 54 includes a cylindrical bore 58, extending through connection portion 32 along axis 56 and opening onto the inner surface 50. Openings 54 also include a partially spherical recess 60, extending from cylindrical bore 58 toward outer surface 52 along axis 56. Openings 54 additionally include a conical portion 62, extending between spherical recess 60 and outer surface 52 along axis 56. Preferably, conical portion 62 is flared outwardly at approximately 45 degrees relative to axis 56.

Each of the connection portions 32 also includes a fastener bore 66 extending between the inner and outer surfaces 50, 52 along transverse axis T and preferably intersecting the longitudinal axis L to thereby position fastener bore 66 intermediate and laterally adjacent bone screw openings 54. Fastener bore 66 is adapted to receive a respective one of the locking fasteners 26 therein. Specifically, fastener bore 66 includes a threaded portion 68 opening onto the inner surface 50 and a conical portion 70 extending between the threaded portion 68 and the outer surface 52. However, it should be understood that other configurations of fastener bore 66 are also contemplated. For example, fastener bore 66 need not necessarily extend entirely through connection portion 32 in that threaded portion 68 can stop short of inner surface 50.

Figure 8:
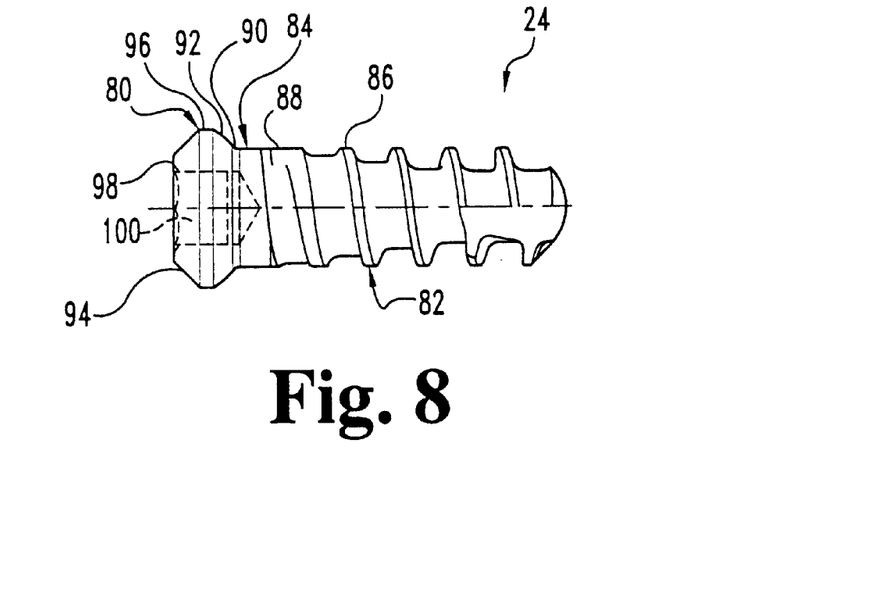
FIG. 8 is a side elevation view of a bone screw according to one aspect of the present invention.

Referring to FIG. 8, shown therein are various details regarding bone screw 24. Bone screw 24 includes a head portion 80 connected to a threaded shank portion 82 by an intermediate portion 84. Threaded shank portion 82 defines a number of threads 86 configured to engage vertebral bone and sized to pass through the cylindrical bore 58 in connection portion 32. Threads 86 are preferably cancellous threads, configured for engagement in the cervical region of the spinal column. Additionally, threads 86 may be configured to be self-tapping. Further, threads 86 preferably define a constant outer diameter along the length of threaded portion 82 approximately equal to the outer diameter of intermediate portion 84, and a root diameter that tapers inwardly toward the intermediate portion 84. However, it should be understood that other configurations of threaded portion 82 are also contemplated as would occur to one of ordinary skill in the art.

The threads 86 gradually transition into intermediate portion 84 by way of a thread run out 88. Intermediate portion 84 has an outer diameter sized somewhat larger than the diameter of the cylindrical bore 58 in connection portion 32. Intermediate portion 84 transitions into head portion 80 by way of a chamfer 90. Head portion 80 includes a lower, partially spherical surface 92 configured to be substantially complementary to the partially spherical recess 60 of opening 54. Head portion 80 also includes an upper conical surface 94, connected to spherical surface 92 by a flattened shoulder 96. In one embodiment, conical surface 94 is flared inwardly relative to shoulder 96 at approximately 45 degrees. Head portion 80 further includes a truncated or flattened upper surface 98, through which extends a tool receiving recess 100 configured to receive a driving tool therein (not shown). In one embodiment, the tool recess 100 is a hexagonal recess; however, other shapes are also contemplated as would occur to those skilled in the art.

Figure 9:
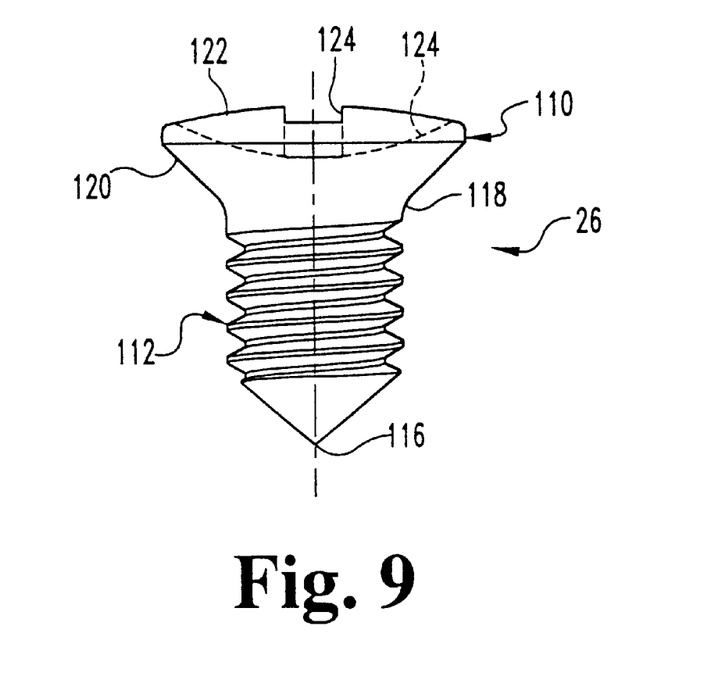
FIG. 9 is a side elevation view of a locking fastener according to another aspect of the present invention.

Referring to FIG. 9, shown therein are various details regarding locking fastener 26. Locking fastener 26 includes a head portion 110 and a threaded shank portion 112 extending therefrom. Threaded shank portion 112 defines a number of machine threads 114, configured to engage the threaded portion 68 of fastener bore 66 in connection portion 32. Threaded shank portion 112 terminates in a sharp point 116 to facilitate insertion of locking fastener 26 into fastener bore 66 and to permit easier penetration into the upper and lower vertebrae $V_u$, $V_l$. Threaded shank portion 112 transitions into head portion 110 by way of an outward taper 118. Head portion 110 includes a lower, conical surface 120 configured substantially complementary to the upper conical surface 94 of bone screw 24. In one embodiment, conical surface 120 is flared outwardly at approximately 45 degrees. Head portion 110 further includes an upper surface 122, through which extends a tool receiving recess 124 configured to receive a driving tool therein (not shown). In one embodiment, the tool recess 124 is a Phillips-type recess; however, other types are also contemplated as would occur to those skilled in the art.

Referring once again to FIGS. 1 and 2, shown therein is spinal stabilization system 20 securely attached to the upper and lower vertebrae $V_u$, $V_l$. Initially, plate 22 is positioned across at least two vertebrae V, with the inner surface 50 of the connection portions 32 placed in abutment against an outer surface of the upper and lower vertebrae $V_u$, $V_l$. The connection portions 32 are then secured to the upper and lower vertebrae $V_u$, $V_l$ by passing bone screws 24 through openings 54 and driving threaded portion 82 into vertebral bone by way of a driver (not shown) inserted in tool receiving recess 100. The bone screws 24 continue to be driven into vertebral bone until the lower spherical surface 92 of the head portion 80 is placed in abutment against the upwardly facing spherical recess 60 of opening 54.

Conical portion 62 of openings 54 serves to facilitate the insertion of bone screws 24 into openings 54. Further, the interaction between spherical surface 92 and spherical recess 60 allows the bone screw 24 to be oriented relative to axis 56 within a range of angles, limited by the interference between the intermediate portion 84 of bone screw 24 and the cylindrical bore 58 in connection portion 32. Openings 54 act as a countersink for the head portion 80 of bone screws 24, allowing a significant portion of head portion 80 to be disposed beneath the upper surface 52 of connection portion 32 to thereby minimize the overall height or profile of plate 22.

After the bone screws 24 are driven into the upper and lower vertebrae $V_u$, $V_l$, thereby securely attaching plate 22 thereto, the locking fasteners 26 are then installed to prevent the bone screws 24 from loosening and backing out. Specifically, the threaded shank portion 112 of fastener 26 is engaged within the threaded portion 68 of fastener bore 66 and threaded therethrough by way of a driver (not shown) inserted in tool receiving recess 124. As the locking fastener 26 is driven through fastener bore 66, point 116 pierces the vertebrae and the threaded portion 68 is driven into vertebral bone, thereby further securing plate 22 to upper and lower vertebrae $V_u$, $V_l$. Additionally, by embedding threaded portion 68 in vertebral bone, the locking fastener 26 is less likely to loosen and back out of fastener bore 66. The locking fastener 26 continues to be driven through the fastener bore 66 until the lower conical surface 120 of head portion 110 engages the upper conical surfaces 94 of the bone screws 24. The abutment of locking fastener 26 against bone screws 24 serves to retain bone screws 24 within openings 54, thereby preventing bone screws 24 from loosening and backing out. In an alternative embodiment of the invention, a washer having a lower conical surface may be disposed between the head portion 110 of locking fastener 26 and the head portion 80 of bone screw 24. Tightening the locking fastener 26 would cause the lower conical surface of the washer to engage the upper conical surface 94 of bone screws 24 to retain the bone screws 24 within the openings 54. An example of such a washer is disclosed in U.S. patent application Ser. No. 09/399,525 entitled "Anterior Cervical Plating System" filed on Sep. 20, 1999, the contents of which have been incorporated by reference.

Figures 10, 11A:
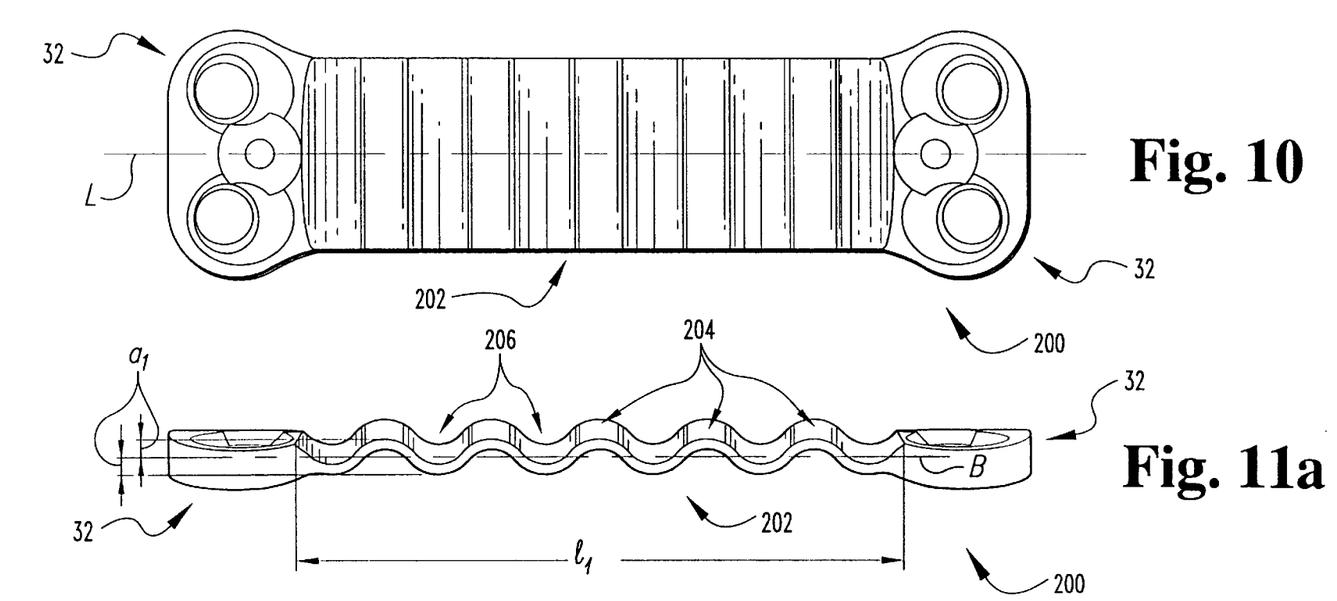
FIG. 10 is a top view of a stabilization plate according to another embodiment of the present invention.
FIG. 11a is a side elevation view of the stabilization plate depicted in FIG. 10, shown in an unstressed configuration.

Referring now to FIG. 10, therein is illustrated a stabilization plate 200 according to another embodiment of the present invention. Stabilization plate 200 extends along a longitudinal axis L. Similar to plate 22, stabilization plate 200 is attached to upper and lower vertebrae $V_U$, $V_L$ by way of a plurality of bone screws 24, and a locking screw 26 that engages the heads of adjacent bone screws 24 to prevent bone screws 24 from loosening and backing out. Further details regarding plate 200 are described more fully below. It should be understood that stabilization plate 200 may be used in any application in which the stabilization plate 22 is used, including those specific applications discussed above.

Stabilization plate 200 includes an elongated central portion 202 and a pair of connecting end portions 32 operably attached to opposite ends of central portion 202, such as by welding, fastening, or by any other method known to one of ordinary skill in the art. However, it should be understood that central portion 202 and connection portions 32 can be formed integral to plate 200, thus forming a unitary structure or construct. Central portion 202 is at least partially formed of a shape-memory material that exhibits pseudoelastic characteristics or behavior at about human body temperature. In one embodiment of the invention, the entire plate 200 is formed of the shape-memory material. However, it should be understood that only central portion 202 need be at least partially formed of the shape-memory material, with the connection portion 32 being formed of any suitable biocompatible material, such as, for example, stainless steel or titanium.

The central portion 202 is at least partially formed of an SMA, such as the SMA described above with regard to plate 22, and has an initial or "memorized" shape or configuration (FIG. 11a), and a different shape or configuration (FIG. 11b) when deformed through the imposition of stress onto plate 200. If the central portion 202 is reshaped or deformed while at a temperature above the transformation temperature $A_S$, the central portion 202 will automatically recover toward its initial shape or configuration when the stress is removed from plate 200. In one embodiment of the present invention, the plate 200 is secured to the upper and lower vertebrae $V_u$, $V_l$ while in a substantially unstressed, initial configuration where virtually all of the SMA material is in an austenitic state. Upon the imposition of stress onto plate 200, caused by relative movement between the upper and lower vertebrae $V_u$, $V_l$, at least a portion of the SMA material is transformed into reversible stress-induced martensite. Upon the reduction or removal of stress, at least a portion of the SMA material is transformed back into austenite. It should be understood that the plate 200 may be pre-stressed prior to being secured to the upper and lower vertebrae $V_u$, $V_l$, thus initially transforming a portion of the SMA material from austenite into SIM. In this case, the SMA material will never attain an entirely austenitic state when the stress imposed onto plate 200 by the upper and lower vertebrae $V_u$, $V_l$ is removed.

Referring specifically to FIG. 11a, central portion 202 is shown in an initial, unstressed configuration. Central portion 202 has a wavy, corrugated shape, defining a series of alternating ridges 204 and grooves 206 extending along longitudinal axis L. Preferably, each of the alternating ridges 204 and grooves 206 is arcuate-shaped so as to form a series of undulating curves extending along longitudinal axis L. Preferably, the ridges 204 and grooves 206 form a sinusoidal pattern relative to the base line B. However, it should be understood that the ridges 204 and grooves 206 can take on other shapes as well, such as, for example, a triangular shape, thus forming a zig-zag pattern, or a square or rectangular shape. When in its initial configuration, central portion 202 has an initial, unstressed length $l_1$, and each of the ridges 204 and grooves 206 defines an initial amplitude $a_1$, as measured from base line B.

Figure 11B:
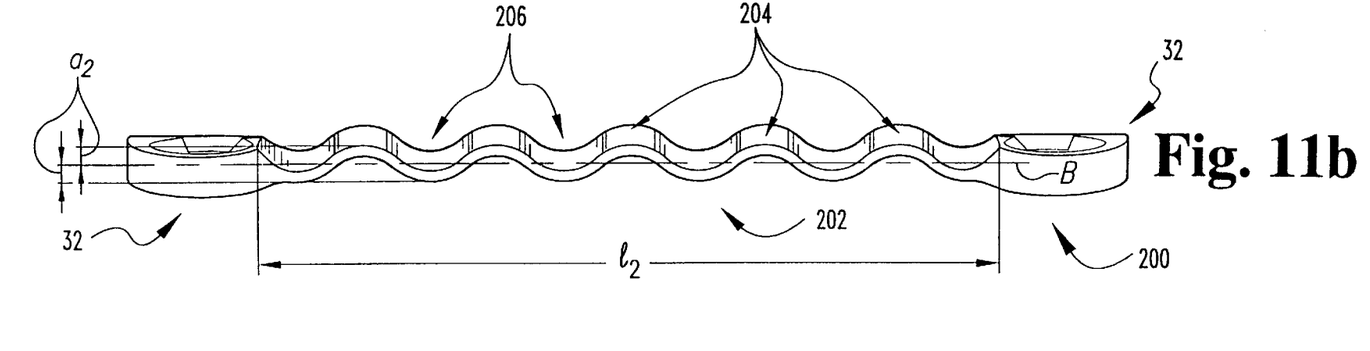
FIG. 11b is a side elevation view of the stabilization plate depicted in FIG. 10, shown in a stressed configuration.

Referring now to FIG. 11b, central portion 202 is shown reformed from the initial shape or configuration illustrated in FIG. 11a to a different, stressed shape or configuration, such reformation occurring in response to the imposition of stress caused by relative displacement between the upper and lower vertebrae $V_u$, $V_l$. This relative displacement can arise through translational movement of upper and lower vertebrae $V_u$, $V_l$, as occurring during either flexion or extension of the spinal column, or through torsional movement, as occurring during rotation of the spinal column. The imposition of stress onto central portion 202 causes at least a portion of the shape-memory material to transform into reversible stress-induced martensite. When deformed into its different configuration, central portion 202 has a different, stressed length $l_2$, and the ridges 204 and grooves 206 have a different amplitude $a_2$. In the illustrated embodiment, central portion 202 is elongated or lengthened when stressed, thus increasing length $l_2$ while decreasing the amplitude $a_2$. However, it should be understood that the central portion 202 could alternatively be compressed or shortened when stressed, thus decreasing length $l_2$ while increasing the amplitude $a_2$.

Referring to FIG. 12, there is illustrated a stabilization system 300 including a pair of spinal rods 302, each extending along a longitudinal axis L and positioned along a portion of the vertebral column on opposite sides of the spine. In the illustrated embodiment, the spinal rods 302 are sized to span a distance between at least two vertebrae V, such as upper and lower vertebrae $V_u$, $V_l$. However, as discussed above with regard to system 20, it should be understood that stabilization system 300 may extend across any number of vertebrae V, including two adjacent vertebrae V. Additionally, although stabilization system 300 is shown attached to the thoracic region of the spine, it should be understood that system 300 may also be utilized in other areas of the spine, such as the cervical, lumbar, lumbo sacral and sacral regions of the spine. Furthermore, although system 300 is shown as having application in a posterior approach, system 300 may alternatively be applied in other surgical approaches, such as, for example, an anterior approach.

Rods 302 are secured to the vertebrae V by a plurality of bone anchors, shown in the form of spinal hooks 304. However, as discussed above with regard to stabilization system 20, other types of bone anchors are also contemplated, such as, for example, bone screws. Anchoring of the hooks 304 to the vertebrae V and connection of the hooks 304 to the spinal rods 302 are well known to those of skill in the art, and therefore need not be discussed in detail. Although rod 302 is illustrated as having a generally circular configuration, it should be understood that other shapes and configurations are also contemplated, such as, for example, an elliptical, square, rectangular or polygonal configuration. Additionally, although rods 302 are illustrated as having a generally straight configuration, it should be understood that rods 302 may take on a curved configuration corresponding to the anatomy of the spinal column.

Spinal rod 302 is at least partially formed of a shape-memory material that exhibits pseudoelastic characteristics or behavior at about human body temperature. In one embodiment of the invention, the entire rod 302 is formed of a shape-memory material. However, it should be understood that only a portion of rod 302 need be at least partially formed of the shape-memory material, with the remainder of rod 302 being formed of any suitable biocompatible material. In one embodiment of the invention, rod 302 is at least partially formed of an SMA, such as, for example, nitinol. However, as discussed above with regard to plate 22, other types of SMA materials are also contemplated as falling within the scope of the invention, such as, for example, other types of shape-memory metal alloys or shape-memory polymers.

Each of the rods 302 has an initial or "memorized" shape or configuration (FIG. 13a), and a different shape or configuration (FIG. 13b) when deformed through the imposition of stress onto rod 302. If the rod 302 is reshaped or deformed while at a temperature above the transformation temperature $A_s$, the rod 302 will automatically recover toward its initial shape or configuration when the stress is removed. In one embodiment of the present invention, the rod 302 is secured to the vertebrae V while in a substantially unstressed, initial configuration, where virtually all of the shape-memory material is in an austenitic state. Upon the imposition of stress onto rod 302, caused by relative movement between the vertebrae V, at least a portion of the shape-memory material will be transformed into reversible stress-induced martensite. Upon the reduction or removal of stress, at least a portion of the shape-memory material is transformed back into austenite. It should be understood that rod 302 may be pre-stressed prior to being secured to the vertebrae V, thus initially transforming a portion of the shape-memory material from austenite into SIM. In this case, the shape-memory material will never attain an entirely austenitic state when the stress imposed onto rod 302 by the vertebrae V is removed.

Figure 13A:
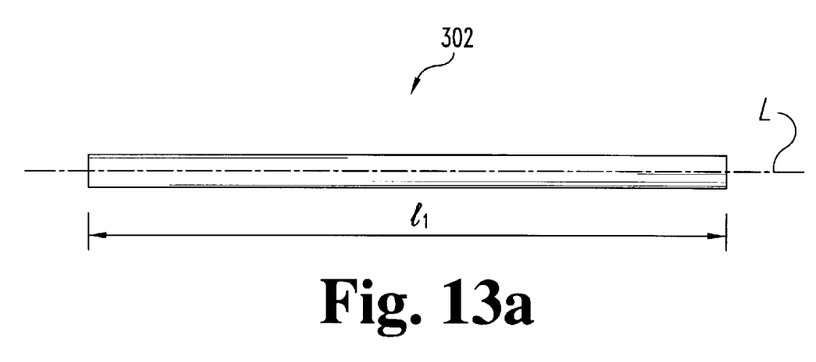
FIG. 13a is a side elevation view of the stabilization rod depicted in FIG. 12, shown in an unstressed configuration.
Figure 13B:
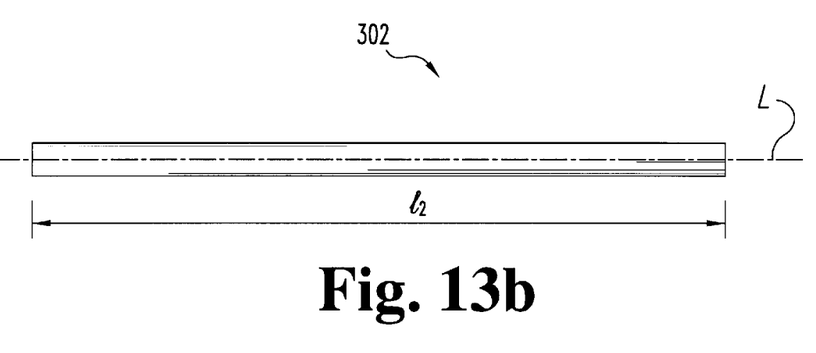
FIG. 13b is a side elevation view of the stabilization rod depicted in FIG. 12, shown in a stresses configuration.

Referring to FIG. 13a, rod 302 is shown in an initial, unstressed configuration. When in its initial configuration, rod 302 has an initial, unstressed length $l_1$. Referring to FIG. 13b, rod 302 is shown reformed from the initial shape or configuration illustrated in FIG. 13a to a different, stressed shape or configuration, such reformation occurring in response to the imposition of stress caused by relative displacement between the vertebrae V. This relative displacement can arise through translational movement of the vertebrae V, as occurring during either flexion or extension of the spinal column, or through torsional movement, as occurring during rotation of the spinal column. The imposition of stress onto rod 302 causes at least a portion of the shape-memory material to transform into reversible stress-induced martensite. When deformed into its different configuration, rod 302 has a different, stressed length $l_2$. In the illustrated embodiment, rod 302 is elongated or lengthened when stressed, thus increasing the overall length of rod 302 from length $l_1$ to length $l_2$. However, it should be understood that rod 302 could alternatively be compressed or shortened when stressed, thus decreasing the overall length of rod 302.

When secured to at least two vertebrae V, stabilization plates 22 and 200 and rods 302 serve to stabilize at least a portion of the spinal column, while allowing at least limited relative displacement or movement between the vertebrae V to restore substantially normal biomechanical function thereto. When secured to the upper and lower vertebrae $V_u$, $V_l$ and stressed in response to relative movement between the upper and lower vertebrae $V_u$, $V_l$, the plates 22, 200 and rods 302 will be reformed from their initial shape or configuration to a different shape or configuration, and at least a portion of the shape-memory material will be transformed from austenite to stress-induced martensite. When in a stress-induced martensitic state, the plates 22, 200 and rods 302 exert a substantially constant restorative force onto the upper and lower vertebrae $V_u$, $V_l$, thereby providing flexible stabilization to the vertebral column, and in particular the cervical region of the spine. Because the plates 22, 200 and rods 302 are at least partially formed of a shape-memory material displaying superelastic or pseudoelastic characteristics, when the stress exerted on plates 22, 200 and rods 302 is reduced or removed, at least a portion of the shape-memory material will transform back into austenite, and the plates 22, 200 and rods 302 will recover toward their initial, memorized shape or configuration. Plates 22, 200 and rods 302 are therefore compliant, capable of being repeatedly transformed between an initial configuration and a different configuration through the imposition and release of stress.

Because the central portions 30, 202 of plates 22, 200 and at least a portion of rod 302 are at least partially formed of a shape-memory material exhibiting pseudoelastic behavior, they are capable of providing a relatively constant restorative forces to the spinal column for correction of various spinal deformities. This pseudoelastic behavior of the shape-memory material allows for a relatively large degree of recoverable deflection or strain of central portion 30, 202 of plates 20, 200 and at least a portion of rod 302 than would be possible with conventional materials, such as stainless steel or titanium. For instance, most conventional materials are capable of being elastically deformed over a relatively small range of deflection or strain, and when further stressed begin to deform plastically. However, shape-memory materials are capable of recovering up to about 8% of deflection or strain, well beyond the yield point of conventional materials.

Moreover, because central portions 30, 202 are each configured to define a number of alternating ridges and grooves along the longitudinal axis L of plates 22, 200, when stress is applied, a greater degree of flexation or deflection is possible than with conventional plates having a flat or rectilinear configuration. The spring-like configuration of central portions 30, 202 allows for this added degree of flexibility or compliability. When central portions 30, 202 are in an initial configuration, each has an initial length and the alternating ridges and grooves have an initial amplitude. However, when stress is applied to plates 22, 200 along the longitudinal axis L, central portions 30, 202 will each be reformed to a different configuration defining a different length and amplitude. When the stress is removed, the spring-like action of the central portions 30, 202 will cause each of central portions 30, 202 to recover toward their initial configuration, length and amplitude. By combining the pseudoelastic characteristics of the shape-memory material with the spring-like configuration of central portions 30, 202, greater degrees of flexation or deflection are possible with stabilization system 20 than are currently possible through existing systems.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. For example, although the systems 20, 300 have been illustrated and described as a spinal stabilization system, it should be understood that plates 22, 200 and rods 302 can also be used as a connector for connecting a first member to a second member, and need not necessarily be used in conjunction with treatment of the spinal column.

What is claimed is:

1. A device for stabilizing at least a portion of a spinal column, comprising:
    a member at least partially formed of a material capable of exhibiting superelastic characteristics at about body temperature and engagable with at least two vertebral bodies by a plurality of anchor members; and
    wherein said member allows at least limited relative displacement between the at least two vertebral bodies; and
    wherein said member is reformed from an initial configuration to a different configuration in response to an imposition of stress caused by said relative displacement between the at least two vertebral bodies.

2. The device of claim 1 wherein said imposition of stress causes at least a portion of said material to form reversible stress-induced martensite, and wherein a reduction of said stress causes at least a portion of said material to form austenite.

3. The device of claim 1 wherein said member is reformed from said different configuration back toward said initial configuration in response to a reduction in said stress.

4. The device of claim 3 wherein reformation of said member back toward said initial configuration occurs without a corresponding change in temperature.

5. The device of claim 1 wherein said member is in an austenitic state when in said initial configuration and in a stress-induced martensitic state when in said different configuration.

6. The device of claim 1 wherein said member has an initial length when in said initial configuration and a different length when in said different configuration.

7. A device for stabilizing at least a portion of a spinal column, comprising:
    a member engagable with at least two vertebral bodies and being at least partially formed of a material exhibiting superelastic characteristics at about body temperature, said member comprising a rod.

8. A device for stabilizing at least a portion of a spinal column, comprising:
    a member at least partially formed of a material exhibiting superelastic characteristics at about body temperature and engagable with at least two vertebral bodies by a plurality of anchor members.

9. The device of claim 8 wherein said material comprises a shape-memory material.

10. The device of claim 9 wherein said shape-memory material comprises a polymer.

11. The device of claim 9 wherein said shape-memory material comprises a metallic alloy.

12. The device of claim 8 wherein said member allows at least limited relative displacement between the at least two vertebral bodies.

13. The device of claim 12 wherein said relative displacement between said at least two vertebral bodies occurs during flexional or extensional movement of said at least a portion of the spinal column.

14. The device of claim 12 wherein said relative displacement between said at least two vertebral bodies occurs during torsional movement of said at least a portion of the spinal column.

15. The device of claim 8 wherein said member comprises a plate.

16. The device of claim 8 wherein said member stabilizes said at least a portion of the spinal column while providing substantially normal biomechanical function thereto.

17. The device of claim 8 further comprising an implant disposable between the at least two vertebral bodies.

18. A method for stabilizing at least a portion of the spinal column, comprising:
providing a member at least partially formed of a material exhibiting superelastic characteristics at about body temperature; and
engaging the member to at least two vertebral bodies.

19. A method for stabilizing at least a portion of the spinal column, comprising:
providing a member at least partially formed of a material capable of exhibiting superelastic characteristics at about body temperature;
engaging the member to at least two vertebral bodies; and
transforming at least a portion of the material into reversible stress-induced martensite as a result of relative movement between the at least two vertebral bodies.

20. The method of claim 19 wherein the transforming is accompanied by a corresponding change in length of the member.

21. The method of claim 20 wherein the change in length of the member is accompanied by a corresponding change in shape of the member.

22. The method of claim 20 further comprising reforming at least a portion of the reversible stress-induced martensite into austenite by reducing the stress.

23. A device for stabilizing at least a portion of a spinal column, comprising:
a rod member engagable with at least two vertebral bodies and being at least partially formed of a shape-memory material capable of exhibiting superelastic characteristics at about body temperature, said rod member having a length that varies in response to relative displacement between the at least two vertebral bodies.

24. The device of claim 23 wherein said variation in length causing at least a portion of said shape-memory material to form reversible stress-induced martensite.

25. The device of claim 23 wherein said length of said rod member increases in response to said relative displacement between said at least two vertebral bodies.

26. The device of claim 23 wherein said rod member is engagable with the at least two vertebral bodies by a plurality of anchor members.

27. The device of claim 23 wherein said rod member stabilizes said at least a portion of a spinal column while providing substantially normal biomechanical function thereto.

28. A device for stabilizing at least a portion of a spinal column, comprising:
a member at least partially formed of a material capable of exhibiting superelastic characteristics at about body temperature; and
a plurality of anchor members adapted to engage said member with at least two vertebral bodies; and
wherein said member allows at least limited relative displacement between the at least two vertebral bodies; and
wherein said member is reformed from an initial configuration to a different configuration in response to an imposition of stress caused by said relative displacement between the at least two vertebral bodies.

29. The device of claim 28 wherein said plurality of anchor members comprise hooks.

30. The device of claim 28 wherein said plurality of anchor members comprise screws.

* * * * *